US012657903B2

(12) United States Patent (10) Patent No.: US 12,657,903 B2
Hatsutani et al. (45) Date of Patent: Jun. 16, 2026

(54) INFORMATION PROCESSING APPARATUS, INFORMATION PROCESSING METHOD, AND INFORMATION PROCESSING PROGRAM FOR SUPPORTING INTERPRETATION OF IMAGES

(71) Applicant: FUJIFILM Corporation, Tokyo (JP)

(72) Inventors: Taro Hatsutani, Tokyo (JP); Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 18/466,000

(22) Filed: Sep. 13, 2023

(65) Prior Publication Data

US 2024/0096086 A1 Mar. 21, 2024

(30) Foreign Application Priority Data

Sep. 21, 2022 (JP) ................................. 2022-150756

(51) Int. Cl.
| | |
|---|---|
| *G06V 10/94* | (2022.01) |
| *G06T 7/00* | (2017.01) |
| *G06T 11/60* | (2026.01) |
| *G06V 10/77* | (2022.01) |
| *G16H 30/40* | (2018.01) |

(52) U.S. Cl.
CPC .......... *G06V 10/945* (2022.01); *G06T 7/0012* (2013.01); *G06T 11/60* (2013.01);
(Continued)

(58) Field of Classification Search
CPC ............. G06V 10/945; G06V 10/7715; G06V 2201/03; G06T 11/60; G06T 2200/24;
(Continued)

(56) References Cited

U.S. PATENT DOCUMENTS

| | | | |
|---|---|---|---|
| 2013/0135305 A1* | 5/2013 | Bystrov | .................... G06T 7/10 |
| | | | 345/420 |
| 2014/0003690 A1* | 1/2014 | Razeto | ................... A61B 6/507 |
| | | | 382/131 |

(Continued)

FOREIGN PATENT DOCUMENTS

| | | |
|---|---|---|
| JP | 2000308619 | 11/2000 |
| JP | 2015149552 | 8/2015 |

(Continued)

OTHER PUBLICATIONS

"Search Report of Europe Counterpart Application", issued on Feb. 8, 2024, pp. 1-7.

(Continued)

*Primary Examiner* — Hai Tao Sun
*Assistant Examiner* — Thomas John Foster
(74) *Attorney, Agent, or Firm* — JCIPRNET

(57) ABSTRACT

An information processing apparatus comprising at least one processor, wherein the processor is configured to: acquire an image; display, on a display, a figure indicating a first region of interest included in the image in a superimposed manner on the image; receive a correction instruction for at least a part of the figure; and specify a second region of interest that at least partially overlaps with the first region of interest based on an image feature of the image and the correction instruction.

10 Claims, 9 Drawing Sheets

(52) U.S. Cl.
CPC ......... *G06V 10/7715* (2022.01); *G16H 30/40*
(2018.01); *G06T 2200/24* (2013.01); *G06T
2207/20081* (2013.01); *G06T 2207/20084*
(2013.01); *G06T 2207/20092* (2013.01); *G06T
2207/30096* (2013.01); *G06V 2201/03*
(2022.01)

(58) Field of Classification Search
CPC . G06T 2207/20081; G06T 2207/20084; G06T
2207/20092; G06T 2207/30096; G06T
2207/10072; G06T 2207/30004; G06T
7/194; G06T 7/11; G16H 30/40
See application file for complete search history.

(56) References Cited

U.S. PATENT DOCUMENTS

| | | | |
|---|---|---|---|
| 2019/0164286 A1* | 5/2019 | Hashizume | G06T 11/60 |
| 2019/0279751 A1 | 9/2019 | Nakamura et al. | |
| 2020/0118274 A1 | 4/2020 | Saito | |
| 2020/0258233 A1* | 8/2020 | Kruecker | G06T 7/73 |
| 2020/0359991 A1* | 11/2020 | Xu | A61B 8/463 |
| 2020/0380673 A1* | 12/2020 | Wang | G06T 7/0012 |
| 2022/0138957 A1 | 5/2022 | Xu et al. | |
| 2022/0405917 A1* | 12/2022 | Madabhushi | G16H 10/40 |
| 2023/0014823 A1* | 1/2023 | Cheng | G06T 7/0004 |
| 2023/0215010 A1* | 7/2023 | Soma | G06T 11/40 |

FOREIGN PATENT DOCUMENTS

| | | |
|---|---|---|
| JP | 2016157291 | 9/2016 |
| JP | 2019153250 | 9/2019 |

OTHER PUBLICATIONS

"Notice of reasons for refusal of Japan Counterpart Application", issued on Mar, 31, 2026, with English transation thereof, pp. 1-8.

\* cited by examiner

FIG. 7

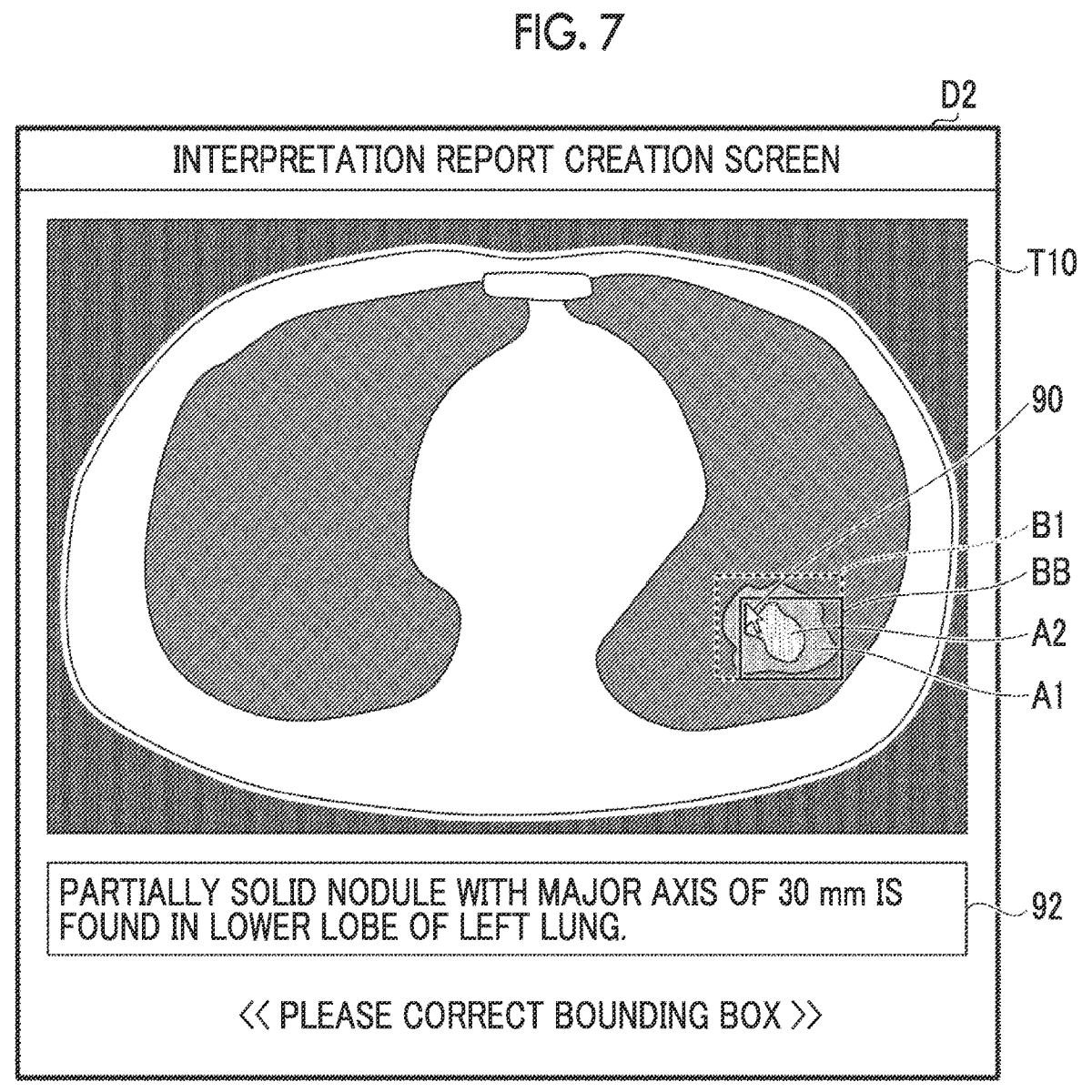

INTERPRETATION REPORT CREATION SCREEN

D2

T10

90

B1
BB
A2
A1

PARTIALLY SOLID NODULE WITH MAJOR AXIS OF 30 mm IS FOUND IN LOWER LOBE OF LEFT LUNG.

<< PLEASE CORRECT BOUNDING BOX >>

92

1

INFORMATION PROCESSING APPARATUS, INFORMATION PROCESSING METHOD, AND INFORMATION PROCESSING PROGRAM FOR SUPPORTING INTERPRETATION OF IMAGES

CROSS-REFERENCE TO RELATED APPLICATIONS

This application claims priority from Japanese Application No. 2022-150756, filed on Sep. 21, 2022, the entire disclosure of which is incorporated herein by reference.

BACKGROUND

Technical Field

The present disclosure relates to an information processing apparatus, an information processing method, and an information processing program.

Related Art

In the related art, image diagnosis is performed using medical images obtained by imaging apparatuses such as computed tomography (CT) apparatuses and magnetic resonance imaging (MRI) apparatuses. In addition, medical images are analyzed via computer aided detection/diagnosis (CAD) using a discriminator in which learning is performed by deep learning or the like, and regions of interest including structures, lesions, and the like included in the medical images are detected and/or diagnosed. The medical images and analysis results via CAD are transmitted to a terminal of a healthcare professional such as a radiologist who interprets the medical images. The healthcare professional such as a radiologist interprets the medical image by referring to the medical image and analysis result using his or her own terminal and creates an interpretation report.

In addition, various methods for supporting the interpretation of medical images have been proposed. For example, JP2019-153250A discloses a technique for creating an interpretation report based on a keyword input by a radiologist and an analysis result of a medical image. In the technique disclosed in JP2019-153250A, a sentence to be included in the interpretation report is created by using a recurrent neural network trained to generate a sentence from input characters.

Further, for example, JP2000-308619A discloses a technique for, in a case of correcting the shape of a region of interest in a medical image, arranging multi-node line segments or point sequences at equal intervals and dragging one of them to follow and move other adjacent multi-node line segments or point sequences in accordance with a predetermined tension.

In the related art, in a case where a region of interest is detected from a medical image via CAD, there is a case that the region of interest may not be detected correctly due to inclusion of an extra peripheral range or omission of detection of a peripheral portion. In the case of using the detected region of interest (for example, in the case of highlighting the region of interest in the medical image, in the case of generating comments on findings regarding the region of interest, and the like), a user is required to manually correct the region of interest to the correct one. However, a technique that can reduce the time and effort in this case is desired. In the technique disclosed in JP2000-308619A, another point adjacent to the dragged point moves in accordance with a predetermined tension, and thus it may be difficult to perform correction accurately in accordance with a correct region of interest.

SUMMARY

The present disclosure provides an information processing apparatus, an information processing method, and an information processing program capable of supporting interpretation of images.

According to a first aspect of the present disclosure, there is provided an information processing apparatus comprising at least one processor, in which the processor is configured to: acquire an image; display, on a display, a figure indicating a first region of interest included in the image in a superimposed manner on the image; receive a correction instruction for at least a part of the figure; and specify a second region of interest that at least partially overlaps with the first region of interest based on an image feature of the image and the correction instruction.

According to a second aspect of the present disclosure, in the above first aspect, the processor may be configured to display, on the display, a figure indicating the second region of interest in a superimposed manner on the image.

According to a third aspect of the present disclosure, in the above first aspect or second aspect, the processor may be configured to receive, as the correction instruction, correction of at least one point of points forming the figure.

According to a fourth aspect of the present disclosure, in the above third aspect, the processor may be configured to specify, as the second region of interest, a region of interest in which at least one point forming the figure after correction is located within a predetermined range from an outer edge of the region of interest among the regions of interest included in the image.

According to a fifth aspect of the present disclosure, in any one of the above first to fourth aspects, the processor may be configured to receive, as the correction instruction, an instruction in a language representing a change in a shape of the figure.

According to a sixth aspect of the present disclosure, in any one of the above first to fifth aspects, the processor may be configured to specify the second region of interest by using a first learning model trained in advance to receive the image, the first region of interest, and the correction instruction as inputs and output the second region of interest.

According to a seventh aspect of the present disclosure, in any one of the above first to fifth aspects, the processor may be configured to: generate a feature map of the image by using a second learning model trained in advance to receive an image as an input and output a feature map of the input image; and specify the second region of interest by using a third learning model trained in advance to receive the feature map, the first region of interest, and the correction instruction as inputs and output the second region of interest.

According to an eighth aspect of the present disclosure, in the above seventh aspect, the processor may be configured to specify the first region of interest based on the feature map.

According to a ninth aspect of the present disclosure, in any one of the above first to eighth aspects, the figure may be at least one of a bounding box, a mask, or a mesh.

According to a tenth aspect of the present disclosure, in any one of the above first to ninth aspects, the image may be a medical image, and the region of interest may be at least one of a region of a structure included in the medical image or a region of a lesion included in the medical image.

According to an eleventh aspect of the present disclosure, there is provided an information processing method comprising: acquiring an image; displaying, on a display, a figure indicating a first region of interest included in the image in a superimposed manner on the image; receiving a correction instruction for at least a part of the figure; and specifying a second region of interest that at least partially overlaps with the first region of interest based on an image feature of the image and the correction instruction.

According to a twelfth aspect of the present disclosure, there is provided an information processing program for causing a computer to execute a process comprising: acquiring an image; displaying, on a display, a figure indicating a first region of interest included in the image in a superimposed manner on the image; receiving a correction instruction for at least a part of the figure; and specifying a second region of interest that at least partially overlaps with the first region of interest based on an image feature of the image and the correction instruction.

With the information processing apparatus, the information processing method, and the information processing program according to the aspects of the present disclosure, it is possible to support the interpretation of images.

BRIEF DESCRIPTION OF THE DRAWINGS

FIG. 7 is a diagram showing an example of a screen displayed on a display.

DETAILED DESCRIPTION

Figure 1:
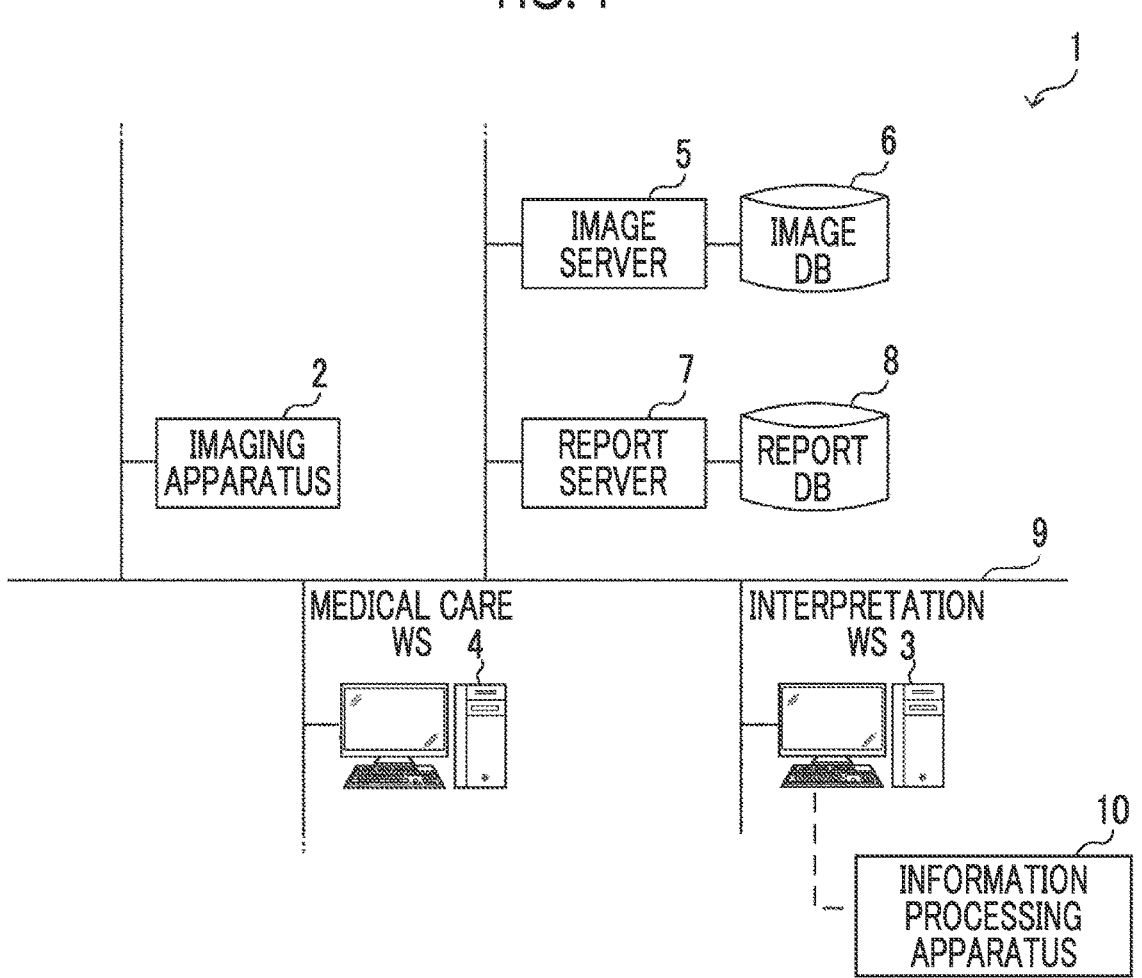
FIG. 1 is a diagram showing an example of a schematic configuration of an information processing system.

Hereinafter, an embodiment of the present disclosure will be described with reference to the drawings. First, a configuration of an information processing system 1 to which an information processing apparatus 10 of the present disclosure is applied will be described. FIG. 1 is a diagram showing a schematic configuration of the information processing system 1. The information processing system 1 shown in FIG. 1 performs imaging of an examination target part of a subject and storing of a medical image acquired by the imaging based on an examination order from a doctor in a medical department using a known ordering system. In addition, the information processing system 1 performs an interpretation work of a medical image and creation of an interpretation report by a radiologist and viewing of the interpretation report by a doctor of a medical department that is a request source.

As shown in FIG. 1, the information processing system 1 includes an imaging apparatus 2, an interpretation work station (WS) 3 that is an interpretation terminal, a medical care WS 4, an image server 5, an image database (DB) 6, a report server 7, and a report DB 8. The imaging apparatus 2, the interpretation WS 3, the medical care WS 4, the image server 5, the image DB 6, the report server 7, and the report DB 8 are connected to each other via a wired or wireless network 9 in a communicable state.

Each apparatus is a computer on which an application program for causing each apparatus to function as a component of the information processing system 1 is installed. The application program may be recorded on, for example, a recording medium, such as a digital versatile disc read only memory (DVD-ROM) or a compact disc read only memory (CD-ROM), and distributed, and be installed on the computer from the recording medium. In addition, the application program may be stored in, for example, a storage apparatus of a server computer connected to the network 9 or in a network storage in a state in which it can be accessed from the outside, and be downloaded and installed on the computer in response to a request.

The imaging apparatus 2 is an apparatus (modality) that generates a medical image showing a diagnosis target part of the subject by imaging the diagnosis target part. Examples of the imaging apparatus 2 include a simple X-ray imaging apparatus, a computed tomography (CT) apparatus, a magnetic resonance imaging (MRI) apparatus, a positron emission tomography (PET) apparatus, an ultrasound diagnostic apparatus, an endoscope, a fundus camera, and the like. The medical image generated by the imaging apparatus 2 is transmitted to the image server 5 and is saved in the image DB 6.

Figure 2:
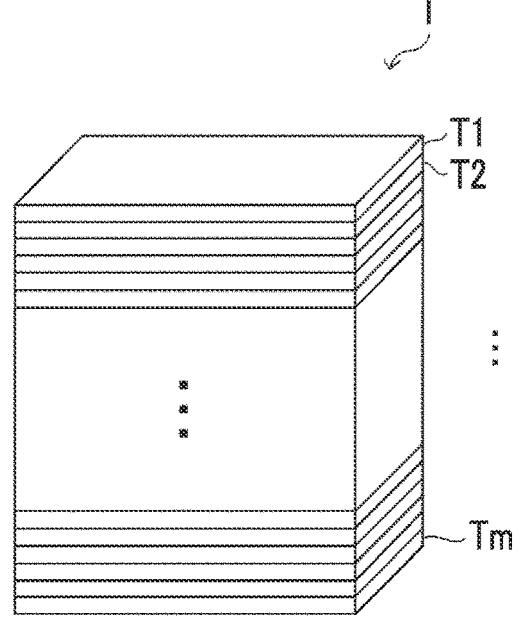
FIG. 2 is a diagram showing an example of a medical image.

FIG. 2 is a diagram schematically showing an example of a medical image acquired by the imaging apparatus 2. A medical image T shown in FIG. 2 is, for example, a CT image consisting of a plurality of tomographic images T1 to Tm (m is 2 or more) representing tomographic planes from the head to the lumbar region of one subject (human body).

Figure 3:
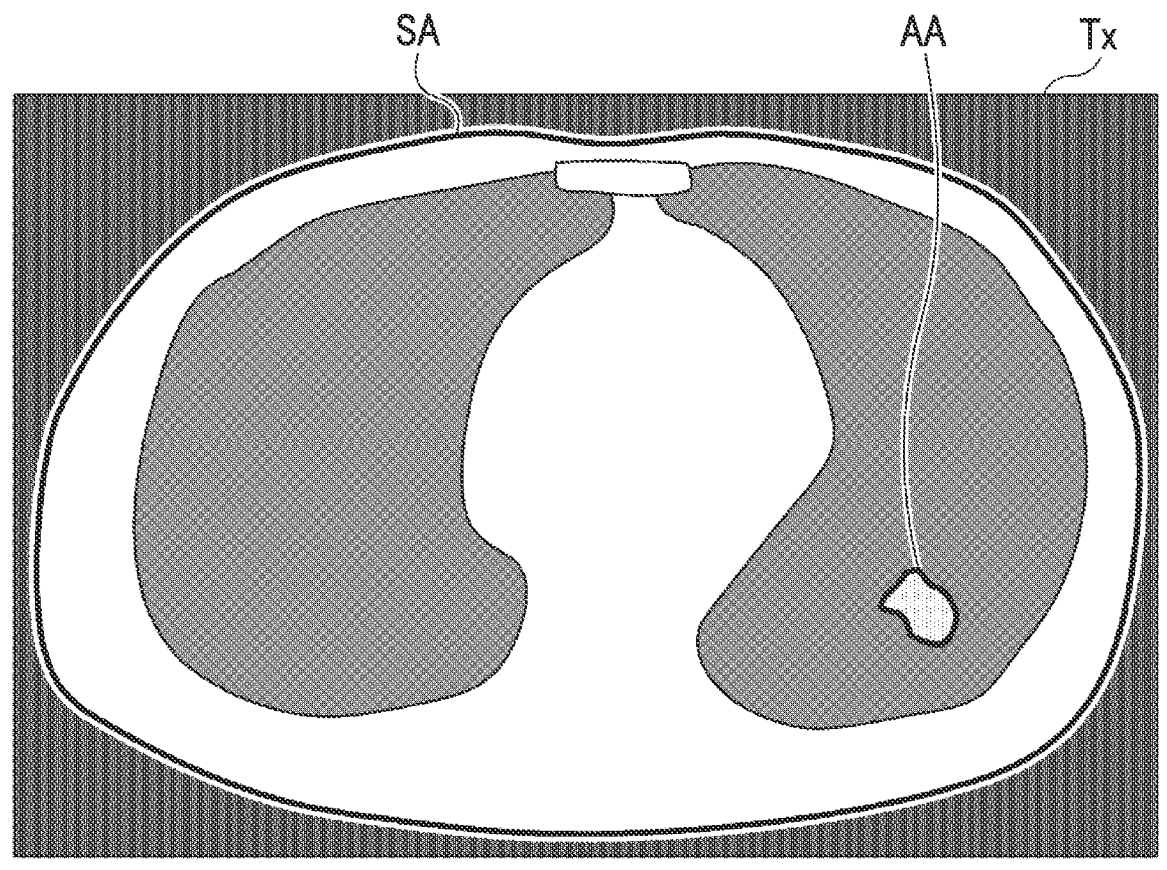
FIG. 3 is a diagram showing an example of a medical image.

FIG. 3 is a diagram schematically showing an example of one tomographic image Tx out of the plurality of tomographic images T1 to Tm. The tomographic image Tx shown in FIG. 3 represents a tomographic plane including a lung. Each of the tomographic images T1 to Tm may include a region SA of a structure showing various organs and viscera of the human body (for example, lungs, livers, and the like), various tissues constituting various organs and viscera (for example, blood vessels, nerves, muscles, and the like), and the like. In addition, each tomographic image may include a region AA of lesions such as, for example, nodules, tumors, injuries, defects, and inflammation. In the tomographic image Tx shown in FIG. 3, the lung region is the region SA of the structure, and the nodule region is the region AA of a lesion. A single tomographic image may include regions SA of a plurality of structures and/or regions AA of lesions. Hereinafter, at least one of the region SA of the structure included in the medical image or the region AA of the lesion included in the medical image will be referred to as a "region of interest".

The interpretation WS 3 is a computer used by, for example, a healthcare professional such as a radiologist of a radiology department to interpret a medical image and to create an interpretation report, and encompasses an information processing apparatus 10 according to the present embodiment. In the interpretation WS 3, a viewing request for a medical image to the image server 5, various image processing for the medical image received from the image server 5, display of the medical image, and input reception of a sentence regarding the medical image are performed. In the interpretation WS 3, an analysis process for medical images, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by, for example, a healthcare professional such as a doctor in a medical department to observe a medical image in detail, view an interpretation report, create an electronic medical record, and the like, and includes a processing apparatus, a display apparatus such as a display, and an input apparatus such as a keyboard and a mouse. In the medical care WS 4, a viewing request for the medical image to the image server 5, display of the medical image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 is connected to the image DB 6. The connection form between the image server 5 and the image DB 6 is not particularly limited, and may be a form connected by a data bus, or a form connected to each other via a network such as a network attached storage (NAS) and a storage area network (SAN).

The image DB 6 is realized by, for example, a storage medium such as a hard disk drive (HDD), a solid state drive (SSD), and a flash memory. In the image DB 6, the medical image acquired by the imaging apparatus 2 and accessory information attached to the medical image are registered in association with each other.

The accessory information may include, for example, identification information such as an image identification (ID) for identifying a medical image, a tomographic ID assigned to each tomographic image included in the medical image, a subject ID for identifying a subject, and an examination ID for identifying an examination. In addition, the accessory information may include, for example, information related to imaging such as an imaging method, an imaging condition, an imaging purpose, and an imaging date and time related to imaging of a medical image. The "imaging method" and "imaging condition" are, for example, a type of the imaging apparatus 2, an imaging part, an imaging protocol, an imaging sequence, an imaging method, the presence or absence of use of a contrast medium, a slice thickness in tomographic imaging, and the like. In addition, the accessory information may include information related to the subject such as the name, date of birth, age, and gender of the subject.

In a case where the image server 5 receives a request to register a medical image from the imaging apparatus 2, the image server 5 prepares the medical image in a format for a database and registers the medical image in the image DB 6. In addition, in a case where the viewing request from the interpretation WS 3 and the medical care WS 4 is received, the image server 5 searches for a medical image registered in the image DB 6 and transmits the searched for medical image to the interpretation WS 3 and to the medical care WS 4 that are viewing request sources.

The report server 7 is a general-purpose computer on which a software program that provides a function of a database management system is installed. The report server 7 is connected to the report DB 8. The connection form between the report server 7 and the report DB 8 is not particularly limited, and may be a form connected by a data bus or a form connected via a network such as a NAS and a SAN.

The report DB 8 is realized by, for example, a storage medium such as an HDD, an SSD, and a flash memory. In the report DB 8, an interpretation report created in the interpretation WS 3 is registered. In addition, the report DB 8 may store findings information regarding the medical image. Findings information includes, for example, information obtained by the interpretation WS 3 through image analysis of a medical image using a computer aided detection/diagnosis (CAD) technology, an artificial intelligence (AI) technology, or the like, and information or the like input by a user after interpreting a medical image.

The findings information indicates, for example, various findings such as a type (name), a property, a position, a measurement value such as a size, and an estimated disease name of a region of interest included in the medical image. Examples of types (names) include the types of structures such as "lung" and "liver", and the types of lesions such as "nodule" and "tumor". The property mainly means the features of the lesion. For example, in the case of a lung nodule, findings indicating absorption values such as "solid type" and "frosted glass type", margin shapes such as "clear/unclear", "smooth/irregular", "spicula", "lobulation", and "serration", and an overall shape such as "round shape" and "irregular shape" can be mentioned. In addition, for example, there are findings regarding the relationship with surrounding tissues such as "pleural contact" and "pleural invagination", and the presence or absence of contrast, washout, and the like.

The position means an anatomical position, a position in a medical image, and a relative positional relationship with other regions of interest such as "inside", "margin", and "periphery". The anatomical position may be indicated by an organ name such as "lung" and "liver", and may be expressed in terms of subdivided lungs such as "right lung", "upper lobe", and apical segment ("S1"). The measurement value is a value that can be quantitatively measured from a medical image, and is, for example, at least one of a size or a signal value of a region of interest. The size is represented by, for example, a major axis, a minor axis, an area, a volume, or the like of a region of interest. The signal value is represented by, for example, a pixel value in a region of interest, a CT value in units of HU, or the like. The estimated disease name is an evaluation result estimated based on the lesion, and, for example, the disease name such as "cancer" and "inflammation" and the evaluation result such as "negative/positive", "benign/malignant", and "mild/severe" regarding disease names and properties can be mentioned.

Further, in a case where the report server 7 receives a request to register the interpretation report from the interpretation WS 3, the report server 7 prepares the interpretation report in a format for a database and registers the interpretation report in the report DB 8. Further, in a case where the report server 7 receives the viewing request for the interpretation report from the interpretation WS 3 and the medical care WS 4, the report server 7 searches for the interpretation report registered in the report DB 8, and transmits the searched for interpretation report to the interpretation WS 3 and to the medical care WS 4 that are viewing request sources.

The network 9 is, for example, a network such as a local area network (LAN) and a wide area network (WAN). The imaging apparatus 2, the interpretation WS 3, the medical care WS 4, the image server 5, the image DB 6, the report server 7, and the report DB 8 included in the information processing system 1 may be disposed in the same medical institution, or may be disposed in different medical institutions or the like. Further, the number of each apparatus of the imaging apparatus 2, the interpretation WS 3, the medical care WS 4, the image server 5, the image DB 6, the report server 7, and the report DB 8 is not limited to the number shown in FIG. 1, and each apparatus may be composed of a plurality of apparatuses having the same functions.

Incidentally, in a case where a region of interest is detected from a medical image via CAD, there is a case that the region of interest may not be detected correctly due to inclusion of an extra peripheral range or omission of detection of a peripheral portion. In the case of using the detected region of interest (for example, in the case of highlighting the region of interest in the medical image, in the case of generating comments on findings regarding the region of interest, and the like), a user is required to manually correct the region of interest to the correct one.

Therefore, the information processing apparatus 10 according to the present embodiment has a function of reducing the time and effort of the correction and supporting the interpretation of the medical image by providing assistance in the case of correcting the region of interest detected from the medical image. The information processing apparatus 10 will be described below. As described above, the information processing apparatus 10 is encompassed in the interpretation WS 3.

Figure 4:
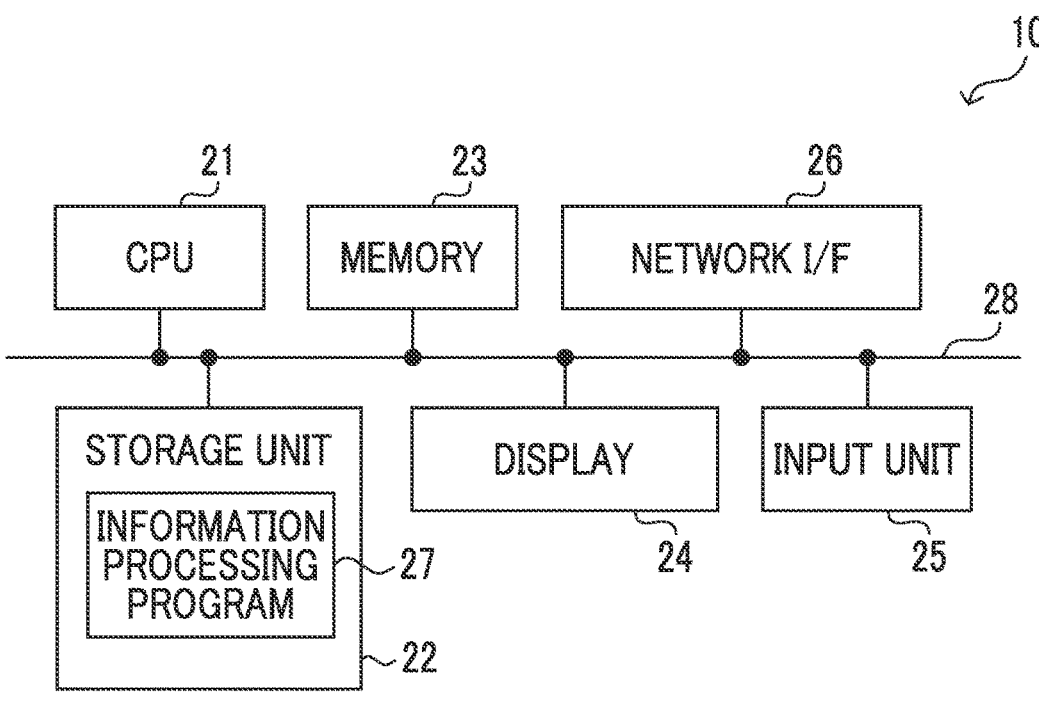
FIG. 4 is a block diagram showing an example of a hardware configuration of an information processing apparatus.

First, with reference to FIG. 4, an example of a hardware configuration of the information processing apparatus 10 according to the present embodiment will be described. As shown in FIG. 4, the information processing apparatus 10 includes a central processing unit (CPU) 21, a non-volatile storage unit 22, and a memory 23 as a temporary storage area. Further, the information processing apparatus 10 includes a display 24 such as a liquid crystal display, an input unit 25 such as a keyboard and a mouse, and a network interface (I/F) 26. The network I/F 26 is connected to the network 9 and performs wired and/or wireless communication. The CPU 21, the storage unit 22, the memory 23, the display 24, the input unit 25, and the network I/F 26 are connected to each other via a bus 28 such as a system bus and a control bus so that various types of information can be exchanged.

The storage unit 22 is realized by, for example, a storage medium such as an HDD, an SSD, and a flash memory. An information processing program 27 in the information processing apparatus 10 is stored in the storage unit 22. The CPU 21 reads out the information processing program 27 from the storage unit 22, loads the read-out program into the memory 23, and executes the loaded information processing program 27. The CPU 21 is an example of a processor of the present disclosure. As the information processing apparatus 10, for example, a personal computer, a server computer, a smartphone, a tablet terminal, a wearable terminal, or the like can be appropriately applied.

Figure 5:
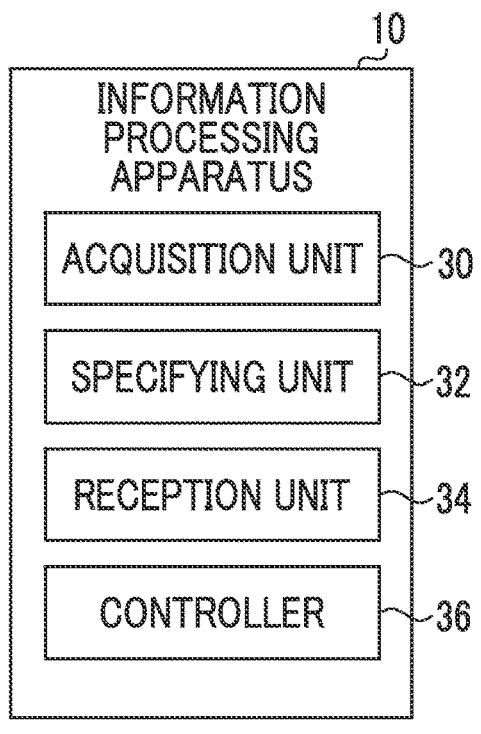
FIG. 5 is a block diagram showing an example of a functional configuration of the information processing apparatus.

Next, with reference to FIGS. 5 to 9, an example of a functional configuration of the information processing apparatus 10 according to the present embodiment will be described. As shown in FIG. 5, the information processing apparatus 10 includes an acquisition unit 30, a specifying unit 32, a reception unit 34, and a controller 36. As the CPU 21 executes the information processing program 27, the CPU 21 functions as respective functional units of the acquisition unit 30, the specifying unit 32, the reception unit 34, and the controller 36.

The acquisition unit 30 acquires a medical image obtained by imaging a subject from the image server 5.

The specifying unit 32 specifies a first region of interest A1 included in the medical image acquired by the acquisition unit 30. As a method for specifying the first region of interest A1, a known method using a CAD technology, an AI technology, or the like can be appropriately applied. For example, the specifying unit 32 may specify a first region of interest A1 from a medical image by using a learning model such as a convolutional neural network (CNN) that has been trained to receive the medical image as an input and specify and output a region of interest included in the medical image.

In addition, the specifying unit 32 may generate a comment on findings regarding the specified first region of interest A1. As a method for generating a comment on findings, a known method using a CAD technology, an AI technology, or the like can be appropriately applied. For example, the specifying unit 32 may generate findings information of the first region of interest A1 by using a learning model such as a CNN that has been trained in advance to receive the region of interest specified from the medical image as an input and output the findings information of the region of interest. After that, the specifying unit 32 may generate a comment on findings including the generated findings information. For example, the specifying unit 32 may generate a comment on findings by using a method using machine learning such as the recurrent neural network described in JP2019-153250A. Further, for example, the specifying unit 32 may generate a comment on findings by embedding findings information in a predetermined template.

Figure 6:
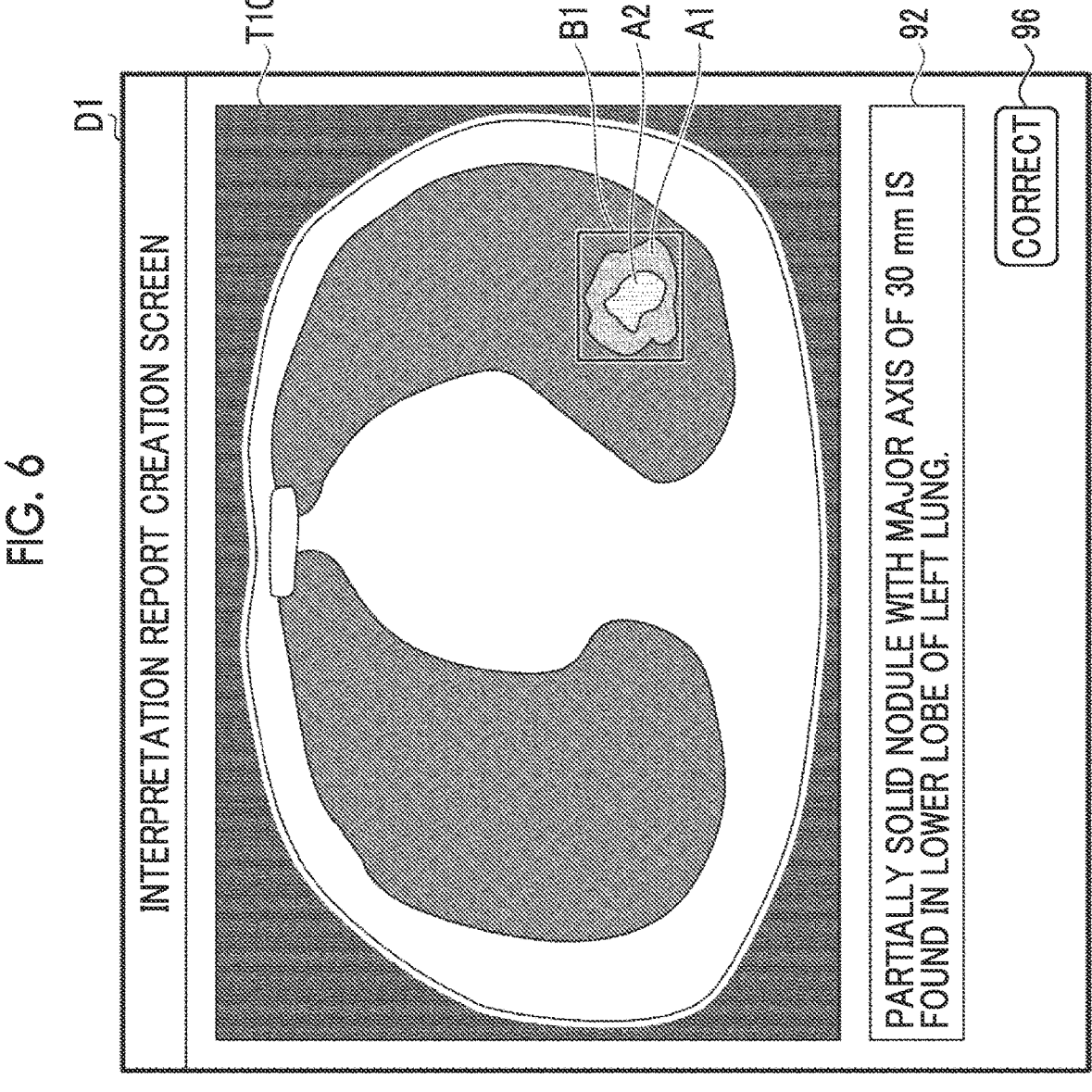
FIG. 6 is a diagram showing an example of a screen displayed on a display.

The controller 36 performs control to display, on the display 24, a figure indicating the first region of interest A1 specified by the specifying unit 32 in a superimposed manner on the medical image acquired by the acquisition unit 30. FIG. 6 shows an example of a screen D1 displayed on the display 24 by the controller 36. The screen D1 includes a medical image T10, in which the first region of interest A1 is emphasized by being surrounded by a bounding box B1. The bounding box B1 is an example of a figure indicating a first region of interest of the present disclosure.

Note that FIG. 6 shows an example in which the bounding box B1 is a rectangle, but the present disclosure is not limited thereto, and the bounding box B1 may be a polygon other than the rectangle. In addition, the figure indicating the first region of interest A1 is not limited to the bounding box B1, and for example, at least one of a mask that changes display methods of colors and the like between the first region of interest A1 and other regions or a mesh that expresses a geometric shape of the first region of interest A1 may be used.

In addition, the controller 36 may perform control to display, on the display 24, a comment on findings regarding the first region of interest A1 generated by the specifying unit 32. The screen D1 of FIG. 6 includes a comment on findings 92 regarding the first region of interest A1.

Here, it is assumed that the user desires to correct the region of interest (correct region of interest) of interest in the medical image T10 of the screen D1 from the first region of interest A1 to a second region of interest A2. In this case, the user selects a correction button 96 on the screen D1 via the input unit 25. In a case where the correction button 96 is selected, the controller 36 transitions to a screen D2 shown in FIG. 7. The screen D2 is a screen for receiving the correction of the figure indicating the first region of interest A1.

The reception unit 34 receives a correction instruction for at least a part of the figure (bounding box B1) indicating the first region of interest A1. Specifically, the reception unit 34 may receive, as a correction instruction, correction of at least one point of points forming the figure indicating the first region of interest A1. The user operates a mouse pointer 90 via the input unit 25, and corrects at least one (the upper left point in FIG. 7) of the points forming the bounding box B1 displayed on the screen D2 to match the second region of interest A2. On the screen D2, the bounding box B1 before the correction is indicated by a dotted line, and a bounding box BB after the correction is indicated by a solid line.

The specifying unit 32 specifies a second region of interest A2 that at least partially overlaps with the first region of interest A1 based on the image features of the medical image acquired by the acquisition unit 30 and the correction instruction received by the reception unit 34. That is, at least a part of the second region of interest A2 need only overlap with the first region of interest A1, and a part of the second region of interest A2 need not overlap with the first region of interest A1. Also, the second region of interest A2 may be smaller or larger than the first region of interest A1. On the other hand, a region of interest that does not overlap at all with the first region of interest A1 is not specified as the second region of interest A2.

Specifically, the specifying unit 32 specifies, as the second region of interest A2, a region of interest in which at least one point forming the figure after correction (bounding box BB) is located within a predetermined range from an outer edge of the region of interest among the regions of interest included in the medical image. In other words, the specifying unit 32 searches a predetermined range from the figure after the correction (bounding box BB) in the medical image, and specifies a region of interest in which at least a part of the outer edge is located within the range as the second region of interest A2. Accordingly, regardless of whether a part or all of the second region of interest A2 that the user desires to specify is encompassed in or protrudes from the figure after correction (bounding box BB), the second region of interest A2 can be appropriately specified.

Figure 8:
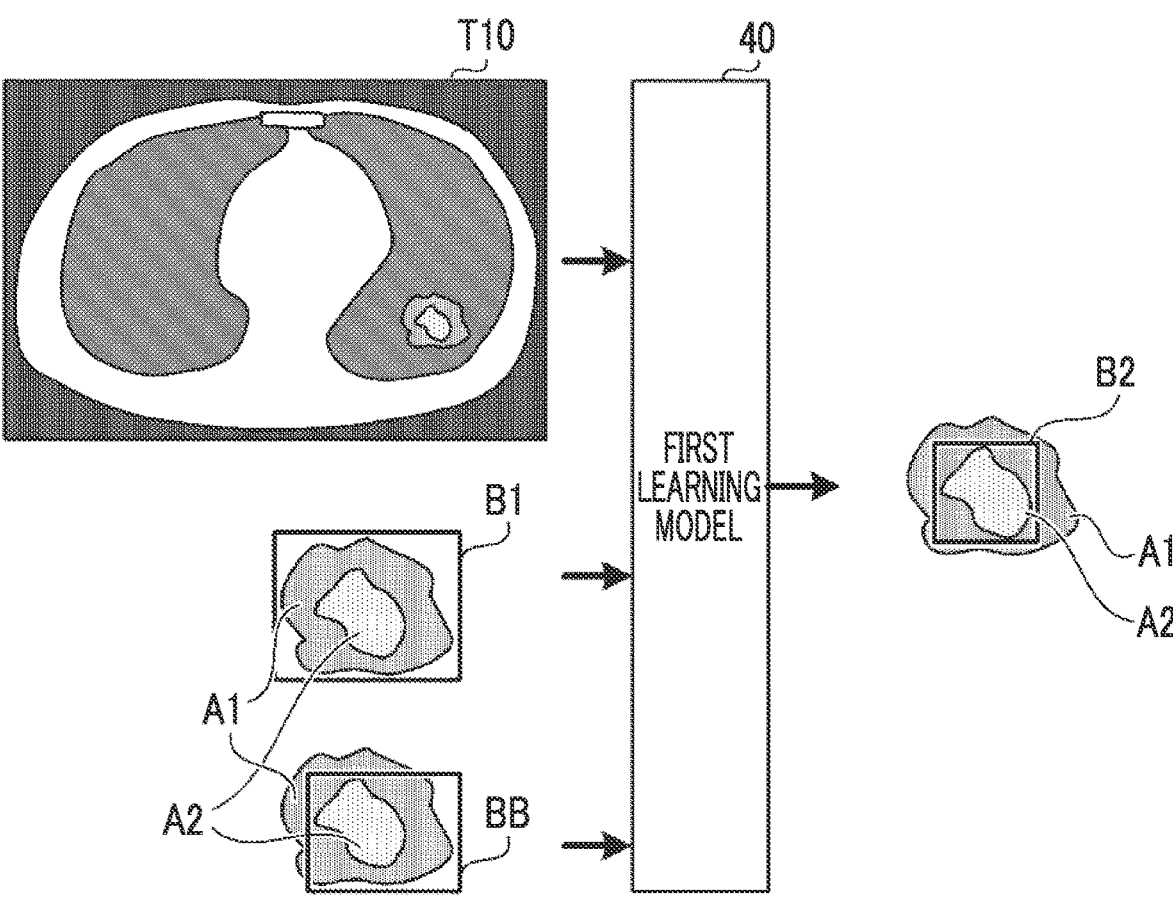
FIG. 8 is a diagram for describing a method of specifying a second region of interest.

For example, as shown in FIG. 8, the specifying unit 32 may specify the second region of interest A2 by using a first learning model 40 trained in advance to receive the medical image, the first region of interest A1, and the correction instruction (bounding box BB) as inputs and output the second region of interest A2. The first learning model 40 is a learning model including a CNN or the like trained using a combination of a medical image, a first region of interest A1 and a correction instruction, and a second region of interest A2 as training data.

In addition, the specifying unit 32 may generate a comment on findings regarding the second region of interest A2 in the same manner as the generation of the comment on findings regarding the first region of interest A1.

Figure 9:
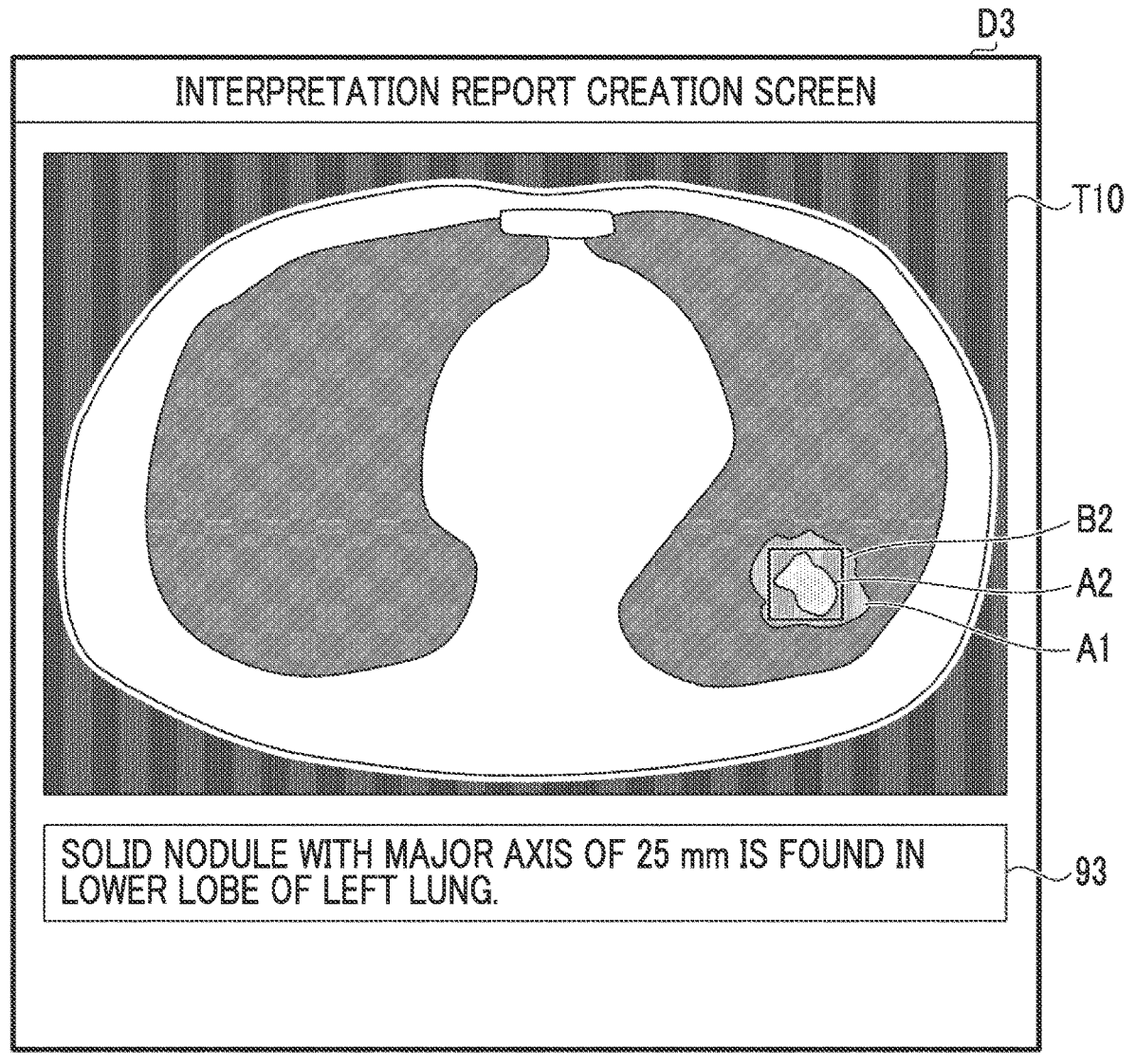
FIG. 9 is a diagram showing an example of a screen displayed on a display.

The controller 36 may perform control to display, on the display 24, a figure indicating the second region of interest A2 specified by the specifying unit 32 in a superimposed manner on the medical image acquired by the acquisition unit 30. FIG. 9 shows an example of a screen D3 displayed on the display 24 by the controller 36. The screen D3 includes a medical image T10, in which the second region of interest A2 is emphasized by being surrounded by a bounding box B2. The bounding box B2 is an example of a figure indicating a second region of interest of the present disclosure.

Note that FIG. 9 shows an example in which the bounding box B2 is a rectangle, but the present disclosure is not limited thereto, and the bounding box B2 may be a polygon other than the rectangle. In addition, the figure indicating the second region of interest A2 is not limited to the bounding box B2, and for example, at least one of a mask that changes display methods of colors and the like between the second region of interest A2 and other regions or a mesh that expresses a geometric shape of the second region of interest A2 may be used.

In addition, the controller 36 may perform control to display, on the display 24, a comment on findings regarding the second region of interest A2 generated by the specifying unit 32. The screen D3 of FIG. 9 includes a comment on findings 93 regarding the second region of interest A2 instead of the comment on findings 92 regarding the first region of interest A1 of the screen D1.

Figure 10:
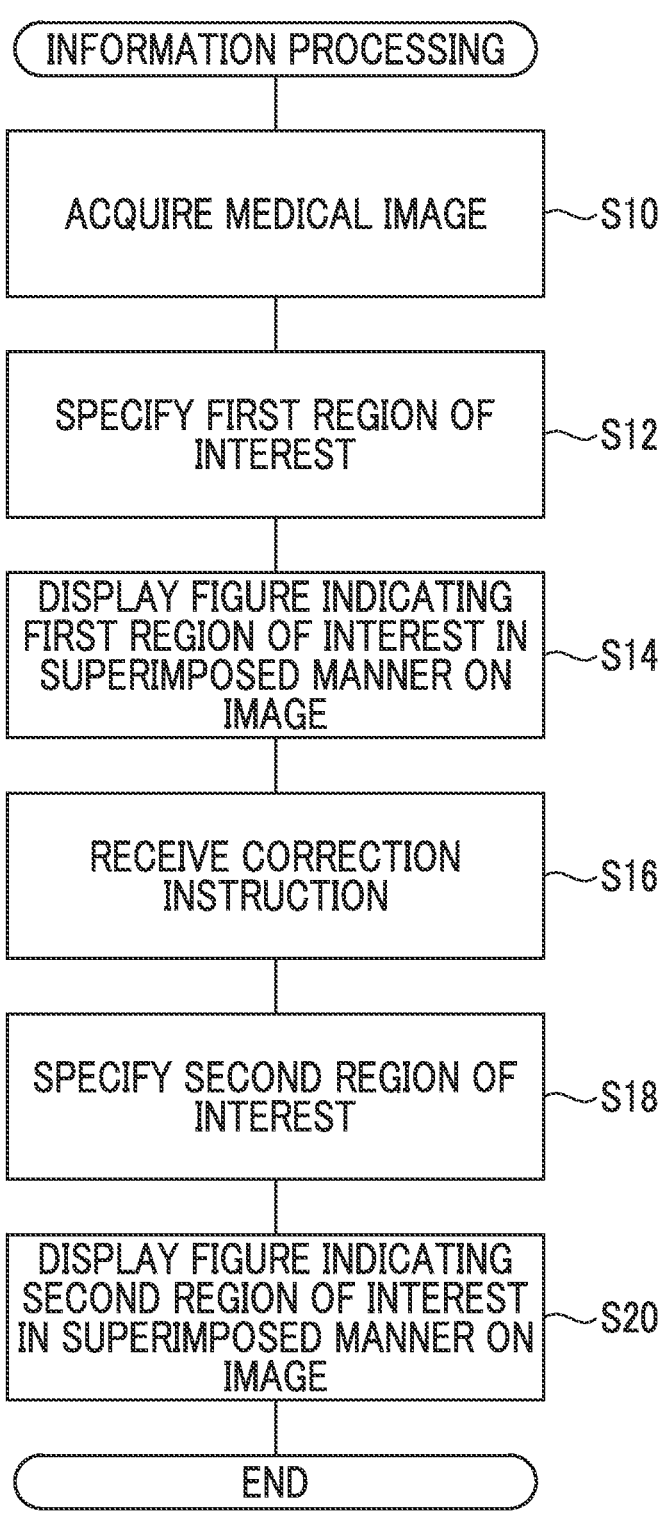
FIG. 10 is a flowchart showing an example of information processing.

Next, with reference to FIG. 10, operations of the information processing apparatus 10 according to the present embodiment will be described. In the information processing apparatus 10, as the CPU 21 executes the information processing program 27, information processing shown in FIG. 10 is executed. The information processing is executed, for example, in a case where the user gives an instruction to start execution via the input unit 25.

In Step S10, the acquisition unit 30 acquires a medical image obtained by imaging a subject from the image server 5. In Step S12, the specifying unit 32 specifies a first region of interest included in the medical image acquired in Step S10. In Step S14, the controller 36 performs control to display, on the display 24, a figure indicating the first region of interest specified in Step S12 in a superimposed manner on the medical image acquired in Step S10.

In Step S16, the reception unit 34 receives a correction instruction for at least a part of the figure indicating the first region of interest displayed on the display 24 in Step S14. In Step S18, the specifying unit 32 specifies a second region of interest that at least partially overlaps with the first region of interest based on the image features of the medical image acquired in Step S10 and the correction instruction received in Step S16. In Step S20, the controller 36 performs control to display, on the display 24, a figure indicating the second region of interest specified in Step S18 in a superimposed manner on the medical image acquired in Step S10, and ends this information processing.

As described above, the information processing apparatus 10 according to one aspect of the present disclosure comprises at least one processor, in which the processor is configured to: acquire an image; display, on a display, a figure indicating a first region of interest included in the image in a superimposed manner on the image; receive a correction instruction for at least a part of the figure; and specify a second region of interest that at least partially overlaps with the first region of interest based on an image feature of the image and the correction instruction.

That is, with the information processing apparatus 10 according to the present embodiment, in a case where the user corrects the first region of interest detected from the image, the second region of interest after correction can be specified based on the image feature in addition to the correction instruction. Therefore, since the second region of interest can be accurately specified while reducing the time and effort for correction, it is possible to support the interpretation of images.

In addition, in the above-described embodiment, the form in which the correction of the figure indicating the first region of interest is received as the correction instruction has been described, but the present disclosure is not limited thereto. For example, the reception unit 34 may receive, as the correction instruction, an instruction in a language representing a change in the shape of the figure indicating the first region of interest. For example, the reception unit 34 may receive inputs such as "larger", "smaller", and "make the margin finer" as phrases representing a change in the shape of the figure indicating the first region of interest.

In this case, for example, the specifying unit 32 may specify the second region of interest by using a learning model trained in advance to receive the medical image, the first region of interest, and the correction instruction in a language as inputs and output the second region of interest. This learning model is a learning model including a CNN or the like trained using a combination of a medical image, a first region of interest and a correction instruction in a language, and a second region of interest as training data. Accordingly, for example, with respect to the correction instruction of "larger", learning is performed such that the figure indicating the second region of interest is larger than the figure indicating the first region of interest. Further, for example, with respect to the correction instruction of "make the margin finer", learning is performed such that the number of vertices of the figure indicating the second region of interest is greater than the number of vertices of the figure indicating the first region of interest.

Further, for example, the specifying unit 32 may predetermine a condition regarding how to change the figure indicating the first region of interest for each correction instruction in a language, and specify the second region of interest based on the condition corresponding to the received correction instruction. For example, with respect to the correction instruction of "larger", a condition is predetermined such that at least one of the vertical width or the horizontal width of the figure indicating the first region of interest is increased. In addition, for example, with respect to the correction instruction of "make the margin finer", a condition is predetermined such that the number of vertices of the figure indicating the first region of interest is increased. In a case where the correction instruction is received by the reception unit 34, the specifying unit 32 refers to a predetermined condition and corrects the figure indicating the first region of interest in accordance with the correction instruction. After that, as described in the above-described embodiment, the specifying unit 32 may specify, as the second region of interest, a region of interest in which at least one point forming the figure after correction is located within a predetermined range from an outer edge of the region of interest among the regions of interest included in the medical image.

Figure 11:
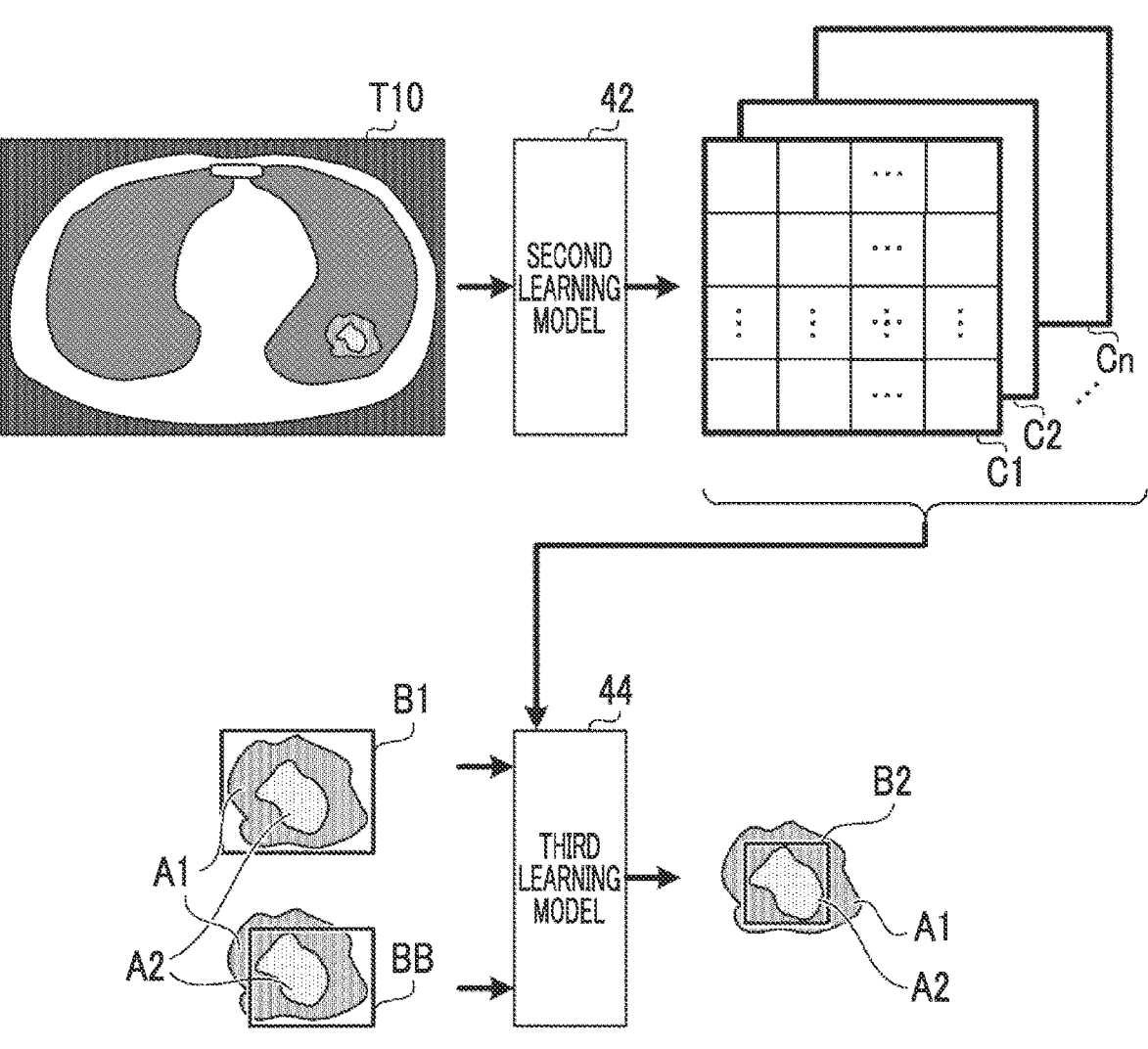
FIG. 11 is a diagram for describing a method of specifying a second region of interest.

In addition, in the above-described embodiment, the form in which the first learning model 40 that receives the medical image, the first region of interest, and the correction instruction as inputs to specify the second region of interest is used has been described, but the present disclosure is not limited thereto. For example, as shown in FIG. 11, the specifying unit 32 may specify the second region of interest by combining two learning models (the second learning model 42 and the third learning model 44). Specifically, first, the specifying unit 32 may generate feature maps C1 to Cn of a medical image by using the second learning model 42 that has been trained in advance to receive the medical image as an input and output the feature maps C1 to Cn of the input medical image. The second learning model 42 is, for example, a model such as a CNN that performs convolution processing using various kernels on the input image, and outputs the feature maps C1 to Cn consisting of feature amount data obtained by the convolution processing. n corresponds to the number of various kernels.

Next, the specifying unit 32 may specify the second region of interest by using a third learning model 44 trained in advance to receive the feature maps C1 to Cn generated by the second learning model 42, the first region of interest, and the correction instruction as inputs and output the second region of interest. The third learning model 44 is, for example, a learning model including a CNN and the like trained using a combination of information of the first region of interest and information of the second region of interest including the correction instruction.

Here, the "information of the first region of interest" used for learning of the third learning model 44 may be, for example, a combination of the feature maps C1 to Cn and a figure (for example, the bounding box B1) indicating the first region of interest or the coordinates of the first region of interest. Further, for example, a partial feature map obtained by editing each of the feature maps C1 to Cn based on this combination may be used, in which a portion of the first region of interest is cut out from each of the feature maps C1 to Cn.

In addition, the "information of the second region of interest" used for learning of the third learning model 44 may be, for example, a combination of the feature maps C1 to Cn and the correction instruction. Further, for example, a partial feature map obtained by editing each of the feature maps C1 to Cn based on this combination may be used, in which a portion corresponding to the correction instruction is cut out from each of the feature maps C1 to Cn.

Note that the specifying unit 32 may also use the second learning model 42 for specifying the first region of interest. For example, the specifying unit 32 may generate feature maps C1 to Cn from the medical image using the second learning model 42, and specify the first region of interest based on the generated feature maps.

Further, in the above-described embodiment, a form assuming interpretation for medical images has been described, but the present disclosure is not limited thereto. The information processing apparatus 10 of the present disclosure can be applied to various images including a region of interest, which are obtained by imaging a subject. For example, the information processing apparatus 10 may be applied to an image acquired using an apparatus, a building, a pipe, a welded portion, or the like as a subject in a non-destructive examination such as a radiation transmission examination and an ultrasonic flaw detection examination. In this case, for example, the region of interest indicates cracks, flaws, bubbles, foreign matter, or the like.

In the above embodiments, for example, as hardware structures of processing units that execute various kinds of processing, such as the acquisition unit 30, the specifying unit 32, the reception unit 34, and the controller 36, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (program).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, as represented by a system on chip (SoC) or the like, there is a form of using a processor for realizing the function of the entire system including a plurality of processing units with one integrated circuit (IC) chip. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

In the above embodiment, the information processing program 27 is described as being stored (installed) in the storage unit 22 in advance; however, the present disclosure is not limited thereto. The information processing program 27 may be provided in a form recorded in a recording medium such as a compact disc read only memory (CD-ROM), a digital versatile disc read only memory (DVD-ROM), and a universal serial bus (USB) memory. In addition, the information processing program 27 may be downloaded from an external device via a network. Further, the technology of the present disclosure extends to a storage medium for storing the information processing program non-transitorily in addition to the information processing program.

The technology of the present disclosure can be appropriately combined with the above-described embodiment and examples. The described contents and illustrated contents shown above are detailed descriptions of the parts related to the technology of the present disclosure, and are merely an example of the technology of the present disclosure. For example, the above description of the configuration, function, operation, and effect is an example of the configuration, function, operation, and effect of the parts according to the technology of the present disclosure. Therefore, needless to say, unnecessary parts may be deleted, new elements may be added, or replacements may be made to the described contents and illustrated contents shown above within a range that does not deviate from the gist of the technology of the present disclosure.

What is claimed is:

1. An information processing apparatus comprising at least one processor, wherein the processor is configured to:
   acquire an image;
   display, on a display, a figure indicating a first region of interest included in the image in a superimposed manner on the image;
   receive a correction instruction for at least a part of the figure;
   input the image into a learning model trained in advance and receive a feature map of the image outputted by the learning model; and input the feature map, the first region of interest, and the correction instruction into another learning model trained in advance and receive a second region of interest, that at least partially overlaps with the first region of interest, outputted by the another learning model, wherein the another learning model is different from the learning model.

2. The information processing apparatus according to claim 1, wherein the processor is configured to display, on the display, a figure indicating the second region of interest in a superimposed manner on the image.

3. The information processing apparatus according to claim 1, wherein the processor is configured to receive, as the correction instruction, correction of at least one point of points forming the figure.

4. The information processing apparatus according to claim 3, wherein the processor is configured to specify, as the second region of interest, a region of interest in which at least one point forming the figure after correction is located within a predetermined range from an outer edge of the region of interest among the regions of interest included in the image.

5. The information processing apparatus according to claim 1, wherein the processor is configured to receive, as the correction instruction, an instruction in a language representing a change in a shape of the figure.

6. The information processing apparatus according to claim 1, wherein the processor is configured to specify the first region of interest based on the feature map.

7. The information processing apparatus according to claim 1, wherein the figure is at least one of a bounding box, a mask, or a mesh.

8. The information processing apparatus according to claim 1, wherein:
   the image is a medical image, and
   the first region of interest and the second region of interest are at least one of a region of a structure included in the medical image or a region of a lesion included in the medical image.

9. An information processing method comprising:
   acquiring an image;
   displaying, on a display, a figure indicating a first region of interest included in the image in a superimposed manner on the image;
   receiving a correction instruction for at least a part of the figure;
   inputting the image into a learning model trained in advance and receive a feature map of the image outputted by the learning model; and
   inputting the feature map, the first region of interest, and the correction instruction into another learning model trained in advance and receiving a second region of interest, that at least partially overlaps with the first region of interest, outputted by the another learning model, wherein the another learning model is different from the learning model.

10. A non-transitory computer-readable storage medium storing an information processing program for causing a computer to execute a process comprising:
   acquiring an image;
   displaying, on a display, a figure indicating a first region of interest included in the image in a superimposed manner on the image;
   receiving a correction instruction for at least a part of the figure;

inputting the image into a learning model trained in advance and receive a feature map of the image outputted by the learning model; and inputting the feature map, the first region of interest, and the correction instruction into another learning model trained in advance and receiving a second region of interest, that at least partially overlaps with the first region of interest, outputted by the another learning model, wherein the another learning model is different from the learning model.

* * * * *